United States Patent [19]

Sleytr et al.

[11] Patent Number: 4,752,395
[45] Date of Patent: Jun. 21, 1988

[54] STRUCTURE WITH MEMBRANES HAVING CONTINUOUS PORES

[76] Inventors: Uwe Sleytr, 10, Parhamerplatz, A-1170 Vienna; Margit Sara, 90/2/24 Vorgartenstr., A-1200 Vienna, both of Austria

[21] Appl. No.: 795,349
[22] PCT Filed: Mar. 8, 1985
[86] PCT No.: PCT/EP85/00089
§ 371 Date: Oct. 28, 1985
§ 102(e) Date: Oct. 28, 1985
[87] PCT Pub. No.: WO85/04111
PCT Pub. Date: Sep. 26, 1985

[30] Foreign Application Priority Data

Mar. 9, 1984 [AT] Austria ................................ A797/84

[51] Int. Cl.$^4$ .......................................... B01D 13/04
[52] U.S. Cl. .................................... 210/490; 210/492; 210/500.38; 55/158; 427/245; 428/315.9
[58] Field of Search .................... 210/490, 492, 500.27, 210/500.37, 500.38, 506; 55/158; 428/315.5, 315.7, 315.9; 427/245

[56] References Cited

U.S. PATENT DOCUMENTS 3,593,852  7/1971  Meriwether ............... 210/500.29 X
3,736,204  5/1973  Meriwether ..................... 210/490 X
3,892,665  7/1975  Steigelmann et al. .............. 210/490

FOREIGN PATENT DOCUMENTS 1237303   3/1967  Fed. Rep. of Germany .
1249517   9/1967  Fed. Rep. of Germany .
1421584  12/1965  France .

OTHER PUBLICATIONS

Morphopoietic & Functional Aspects of Regular Protein Membranes Present on Prokaryotic Cell Walls by: U. B. Sleytr, pp. 1 to 25.
Self-Assembly of the Hexagonally & Tetragonally Arranged Subunits of Bacterial Surface Layers and Their Reattachment to Cell Walls by: U. Sleytr, pp. 360-377.
The Dynamic Process of Assembly of Two-Dimensional Arrays of Macromolecules on Bacterial Cell Walls by: U. B. Sleytr & R. Plohberger, pp. 36-47.
Archives of Microbiology, 1986 by U. Sleytr et al., pp. 19-24.
Dorset et al., "Two-Dimensional Crystal Packing of Matrix Porin . . ." J. Mol. Biol 1983, 165(4) 701-710.
Garavito et al., "X-Ray Diffraction . . ." Chemical Abstracts, vol. 98, No. 17, Apr. 25, 1983, p. 218 Abstract 139218u.
Sleytr et al. "Structural and Chemical . . ." Arch. Microbiology (1986) 146: pp. 19-24.
Engel et al. "Porin Channel Triplets . . .", Nature, vol. 317 (10/17/85) pp. 643-645.
Garavito et al. "X Ray Diffraction . . ." J. Mol. Biol. (1983) 164 pp. 313-327.
Sleytr et al. "Ultrafiltration Membranes with . . ." Appl Microbiol Biotechnol (1986) 25: pp. 83-90.
Bretscher "The Molecules of the Cell Membrane" Science, Oct. 1985, vol. 253, No. 4, pp. 86-90.
Sára et al. "Production and Characteristics . . ." J Membrane Science 33(1987) pp. 27-49.

Primary Examiner—Richard V. Fisher
Assistant Examiner—W. Gary Jones
Attorney, Agent, or Firm—Bierman & Muserlian

[57] ABSTRACT

A structure usable as an ultrafiltration membrane has membranes (20) with continuous pores which are linked to or into an appropriately porous carrier (21). Each of these membranes (20) consist of protein molecules or protein containing molecules arranged according to a two-dimensional crystal lattice, between which continuous pores of equal size and form remain free, and they are advantageously formed from molecules, which were particularly separated from cell-membranes of procaryons, by means of a recrystallization process designated as self-organization, and which are preferably deposited on or into the carrier (21) and are cross-linked with the carrier (21) intra- or intermolecularly, respectively, through foreign molecules.

The structure is suitable, furthermore, for use as a separating organ for a gas separation or for an ion exchange process, as well as for use as a carrier structure for other semi-permeable membranes, such as hyperfiltration membranes. Moreover, with membranes in vesicle form it can serve as a chromatography column and, in the form of film, as envelope material for the most varied substances.

36 Claims, 6 Drawing Sheets

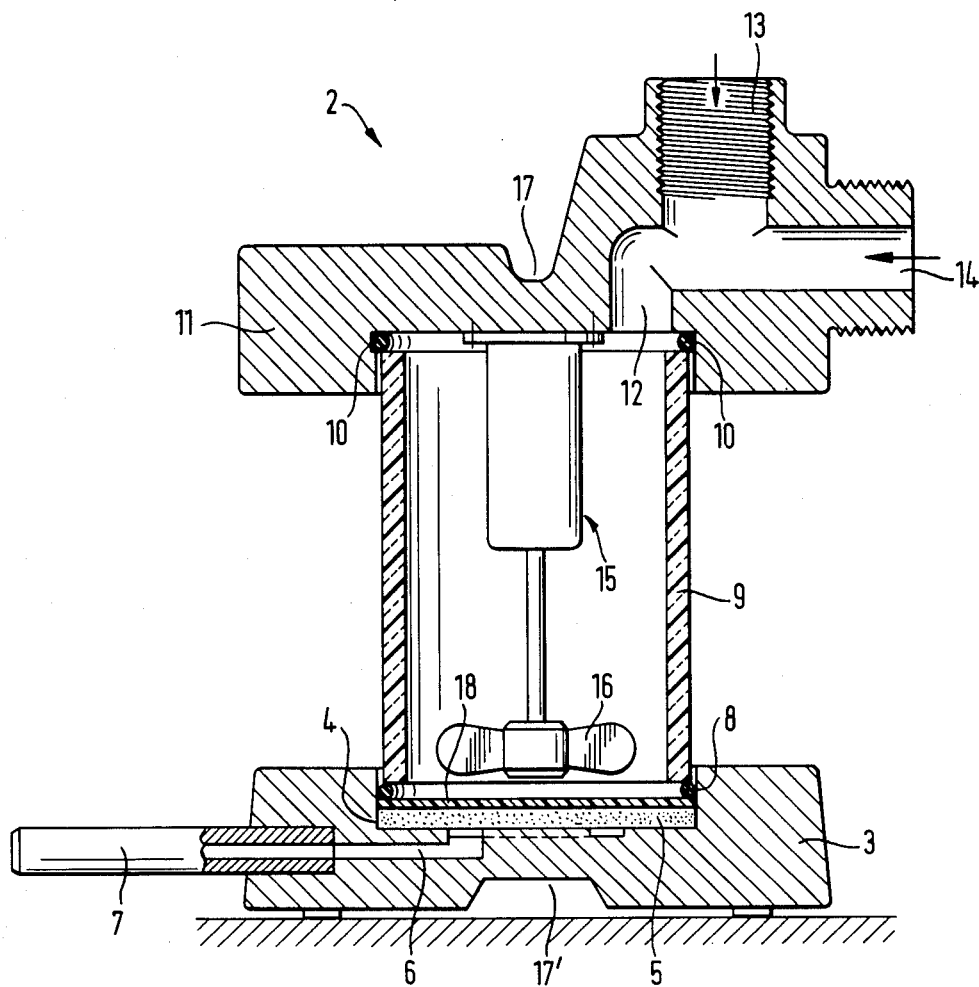

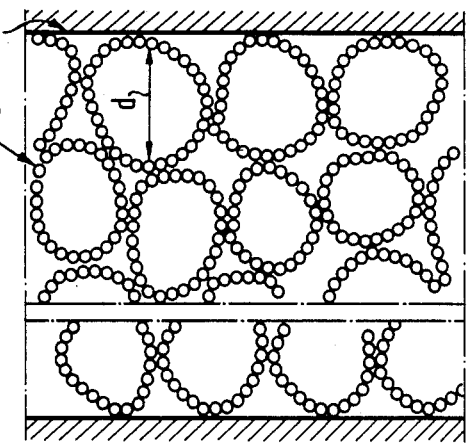
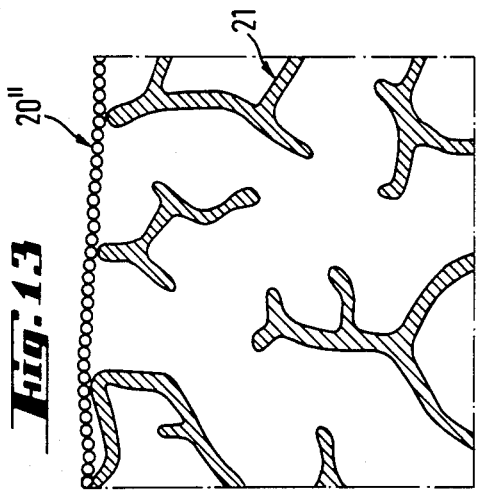
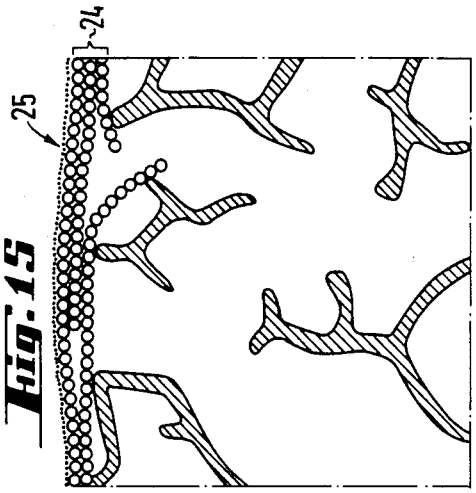
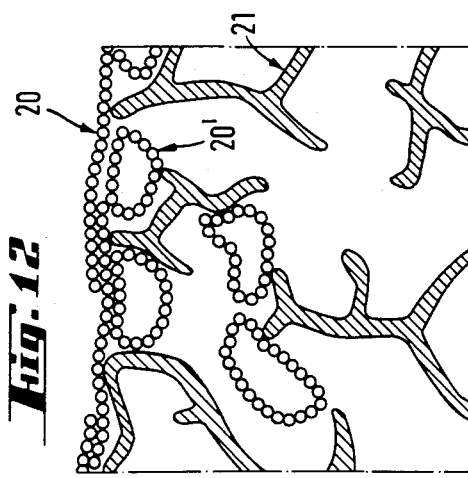
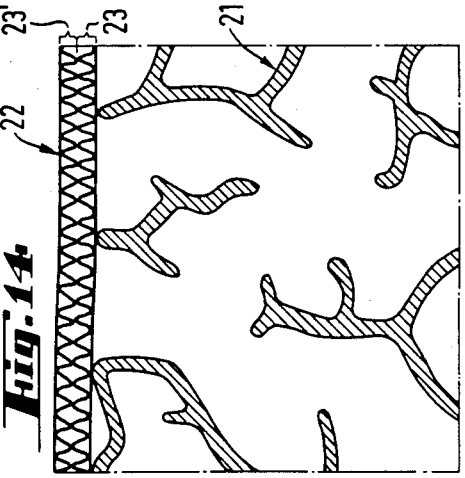

STRUCTURE WITH MEMBRANES HAVING CONTINUOUS PORES

TECHNICAL DOMAIN

The invention is concerned with a structure which comprises at least one membrane with continuous pores, or which is formed by at least one such membrane, with said pores being particularly within the diameter range of 2 to 200 nm (nanometers) In addition, it concerns a method for the production of this structure, as well as several advantageous applications of said structure.

STATE OF THE ART

Structures with membranes that have continuous pores within a diameter range of 2 to 200 nm are, e.g., ultrafiltration membranes used in processes for the fractionation or concentration of mixtures of high-molecular organic substances with different molecular weights. Asymmetrical ultrafiltration membranes are now used in many instances for industrial and semi-industrial purposes; they are comprised of a very thin separating film which is determinative for the mass transfer through the membrane and for the selectivity of separation, and which in general is between 100 and 200 nm thick, and of a coarsely porous support layer. The separating films consist of various polymers, preferably of cellulose derivatives or polysulfones. Such ultrafiltration membranes are either phase inversion membranes or composite membranes. In phase inversion membranes, a homogeneous polymer solution is brought into contact with a precipitant, whereupon, at the polymer solution/precipitant contact surface, the membrane is formed, in which latter the coarsely porous support film is joined to the finely porous film. In composite membranes, the separating film and the support film are produced separately and joined together only subsequently.

In the known ultrafiltration membranes, the pore diameter does not have a fixed size, but the diameters of the pores vary, randomly distributed around a mean value. This behavior of the ultrafiltration membrane is characterized by its grade efficiency curve. To determine this grade efficiency curve, the R portion, which is retained by the ultrafiltration membrane during filtration, is determined, in %, for various ideal test molecules (these are spherical molecules in not charged state) with varied molecular weights (MW). The grade efficiency curve itself represents an interpolation of these test values and shows the relationship of the relative retained quantity (R) to the logarithm of the molecular weight log ←(MW).

FIG. 1 shows a diagram with the grade efficiency curves for three commercially available ultrafiltration membranes, namely:

Curve A for the PSED 25 (Millipore) membrane of Messrs. Millipore, Bedford, Mass., U.S.A.,
Curve B for the PSVP 1000 (Millipore) membrane of the same firm, and
Curve C for the PM 30 (Amicon) membrane of Messrs. Amicon, Danvers, Mass., U.S.A.

As can be seen from these grade efficiency curves, it is not possible to effect with the aid of these ultrafiltration membranes any sharp separation of molecules with slightly different molecular weights.

A further characteristic value for the performance of an utrafiltration membrane is the so-called flow rate. This is the quantity of water which flows through the membrane per m$^2$ per hour at a set operating overpressure prevailing between both sides of the membrane. In the known phase inversion membranes, whose separating films are about 100–200 nm thick, the membrane develops considerable resistance to the water flowing through. The flow rate is higher, the higher the number of pores per unit of area of the membrane, or the lesser the effective pore depth, i.e. the length of the canals forming the pores. Additional important quality features of ultrafiltration membranes is also their chemical and/or thermal stability.

DESCRIPTION OF THE INVENTION

The invention has the task of indicating a structure which comprises at least one membrane with continuous pores or is formed of at least one such membrane, wherein said pores are within a diameter range of 1 to 8 nm and where, in its application as an ultrafiltration membrane, sharp separation can be realized, if necessary, between molecules with slightly different molecular weights, and with which ultrafiltration membrane it is furthermore possible to attain a higher flow rate than with known ultrafiltration membranes, and which has good chemical and thermal stability.

The task assigned to the invention is solved in the structure according to the invention in that the membrane or the membranes which extend along plane, curved, cylindrical or vesicular surfaces, are in each case constructed of at least one layer of contiguous molecules joined together and thereby arranged according to a crystal lattice, namely protein molecules or protein containing molecules, whereby in these layers, pores arranged according to a lattice remain free between the molecules, and wherein the membranes are linked to or combined within an appropriately porous carrier, or are joined into an unsupported film. In these membranes, the protein molecules or protein containing molecules are advantageously joined into a single layer or into several contiguous layers, in each case arranged according to a lattice, with the contiguous protein molecules or protein containing molecules in these layers preferably being joined to each other by secondary valence compounds.

According to an advantageous embodiment of the invention, the structure according to the invention is characterized in that mono- or bifunctional foreign molecules are linked to reactive groups of the protein molecules or protein containing molecules, which advantageously can be carboxyl groups and/or amino groups and/or sulfhydryl groups and/or hydroxyl groups, wherein the structure advantageously exhibits membranes with layers of protein molecules or protein containing molecules, within which the same foreign molecules are linked to essentially all these molecules at the same reactive places.

According to a further advantageous embodiment of the structure according to the invention, it is characterized in that protein molecules or protein containing molecules of the membranes are intramolecularly covalently cross-linked through bifunctional foreign molecules, and/or in that it has membranes on which contiguous or neighboring protein molecules or protein containing molecules, which belong to the same membrane or to two contiguous or neighboring membranes, are covalently cross-linked to one another—appropriately through bifunctional foreign molecules, and/or in which protein molecules or protein containing molecules are cross-linked with the carrier material—appropriately through bifunctional foreign molecules.

In yet another advantageous embodiment of the structure according to the invention, it is characterized in that the foreign molecules reach into the zone of the membrane pores recessed between the protein molecules or the protein containing molecules.

Pursuant to a last advantageous embodiment, the structure according to the invention is characterized by membranes, whose protein molecules or protein containing molecules and/or foreign molecules linked to them dissociate and thereby can accept predetermined electric charges, depending on these working conditions. Insofar as the type and/or distribution of these dissociable groups at the membrane is concerned, these membranes are advantageously constructed asymmetrically with regard to each surface parallel to the membrane extension.

The invention has the additional task of indicating a method for producing a structure which comprises at least one membrane with continuous pores, and in particular, a method for producing the structure according to the invention.

This problem is solved in the method according to the invention, wherein protein molecules or protein containing molecules obtained from cell-membranes, appropriately cell-membranes of prokaryons, or fragments of layers of such molecules, which are linked contiguous to each other in these layers, are brought into solution or suspension, respectively, in a liquid, appropriately aqueous medium that appropriately contains chaotropic agents, such as guanidine hydroxide or urea and/or surfactants, and wherein subsequently, appropriately through a reduction of the concentration of the chaotropic agents and/or surfactants and/or through changing the pH-value, conditions are created in the medium at which the protein molecules or protein containing molecules and/or the layer fragments then combine through self-organization into membranes, in which the protein molecules or the protein containing molecules are arranged contiguously according to a crystal lattice, whereat pores arranged between the molecules according to a lattice remain free, and wherein the membranes so formed are placed in, respectively, on a carrier, and wherein, appropriately through treatment with mono- and/or bifunctional foreign molecules, protein molecules or protein containing molecules of the membranes are substituted at their reactive groups, and/or are cross-linked through these reactive groups intramolecularly and/or with each other and/or with the carrier. To produce the solution or suspension, respectively, of the protein molecules or protein containing molecules and/or layer fragments built up of such molecules, an appropriately aqueous suspension is produced advantageously of cell-membranes of such a type, as have external layers built up from contiguous protein molecules or protein containing molecules joined to each other and arranged according to a crystal lattice, whereat pores arranged according to a lattice between the molecules in these layers remain free, whereupon, appropriately through adding chaotropic agents and/or surfactants and/or through modifying the pH-value in the medium, said protein molecules or protein containing molecules or fragments of the layers consisting of these molecules are separated from the cell-membranes, and wherein the remnants of the cell-membranes are separated from the medium.

Pursuant to advantageous embodiments of the method according to the invention, the separation of the protein molecules or protein containing molecules is advantageously effected through increasing the pH-value from about 7.0 to a value lesser than or equal to 13.0, but in particular to a value lesser than or equal to 9.5, or by reducing the pH-value from about pH 7.0 to a value greater than or equal to 1.0, but in particular to a value greater than or equal to 2.5.

Pursuant to another advantageous embodiment of the invention, the method according to the invention is characterized in that the reduction of the concentration of chaotropic agents and/or surfactants and or the change of the pH-value to be carried through for inducing the self-organization of the protein molecules or the protein containing molecules and/or the separated layer fragments into membranes, takes place by means of a dialysis.

In a further advantageous embodiment of the invention, the method according to the invention is characterized in that the mono- and/or bifunctional foreign molecules exhibit groups which react with carboxyl groups, amino groups, sulfhydryl groups or hydroxyl groups of the protein molecules or protein containing molecules.

Pursuant to another advantageous embodiment of the method according to the invention, the self-organization of the protein molecules or protein containing molecules and/or layer fragments into membranes takes place at a solid-to-liquid phase boundary.

Pursuant to a further advantageous embodiment of the invention, the method according to the invention is characterized in that membranes formed through the self-organization of the protein molecules or protein containing molecules and/or layer fragments, have practically all maximum area dimensions of less than 100 $\mu$m, however preferably less than 15 $\mu$m.

In a last advantageous embodiment of the method according to the invention, the placing of the membranes at or in a porous carrier, respectively, is effected through depositing on the carrier.

Lastly, the invention comprises the following applications according to the invention of the structure according to the invention or of the structure produced pursuant to the method according to the invention, to wit, the utilization of the structure as an ultrafilter, or as a separating organ for a gas separation, or as a separating organ for an ion exchange process;

the utilization of the structure as a carrier for other semipermeable membranes, which stretch over pores of the membranes of the structure, wherein, appropriately, these other semipermeable membranes are cross-linked with protein molecules or protein containing molecules of the membranes of the structure through their carboxyl groups and/or amino groups and/or sulfhydryl groups and/or hydroxyl groups, directly or through bifunctional foreign molecules. These other semipermeable membranes can advantageously be: hyperfiltration membranes, appropriately surfactant- or surfactant-like lipoid hyperfiltration membranes, or separating organs for a gas separation, or separating organs for an ion exchange process, or separating organs for a pervaporation process, or solution diffusion membranes;

utilization as a separating column for penetration-chromatography, in which the membranes are appropriately shaped as vesicles;

utilization as an envelope material for substances, where the envelope material can advantageously be used as a biologically degradable packaging material, or as capsule-envelope for pharmaceutical preparations to be administered orally.

BRIEF DESCRIPTION OF THE DRAWINGS

FIG. 5 shows a pressure unit for production of the ultrafilter.

FIG. 10-16 show sectional views of variant structures.

DESCRIPTION OF THE PREFERRED EMBODIMENTS

The cell-membranes of some prokaryons, in particular of some bacilli, have an external layer, the surface topography of which, as determined by an electron microscope, has a periodicity which permits the conclusion that the layer has a crystalline structure. This external layer, hereinfollowing called the S-layer (=surface layer), can be separated from the subjacent layer containing peptidoclycan of the cell-membrane in an aqueous medium by adding chaotropic agents, and brought into a solution. As can be determined by biochemical methods, these S-layers in most cases consist of identical molecules, namely protein molecules or protein containing molecules. If the concentration of these chaotropic agents in the solution is reduced, e.g., by dialysis, then small membrane fragments will be formed from these molecules through self-organization, with surface dimensions of up to about 10 to 15 $\mu$m, which exhibit the same surface topography as the original S-layer. These membrane fragments are hereinfollowing called P-membranes. Furthermore, since at an additional increase of the concentration of the chaotropic agents, such P-membranes will decompose again, and will again form as P-membranes during a renewed reduction of the concentration, it is assumed that the P-membranes are built up of layers of contiguous, joined together molecules or protein molecules arranged according to a crystal lattice, and that the reversibly soluble and reconstitutable linking of the molecules in the P-membranes takes place through secondary valences of these molecules.

Figure 1:
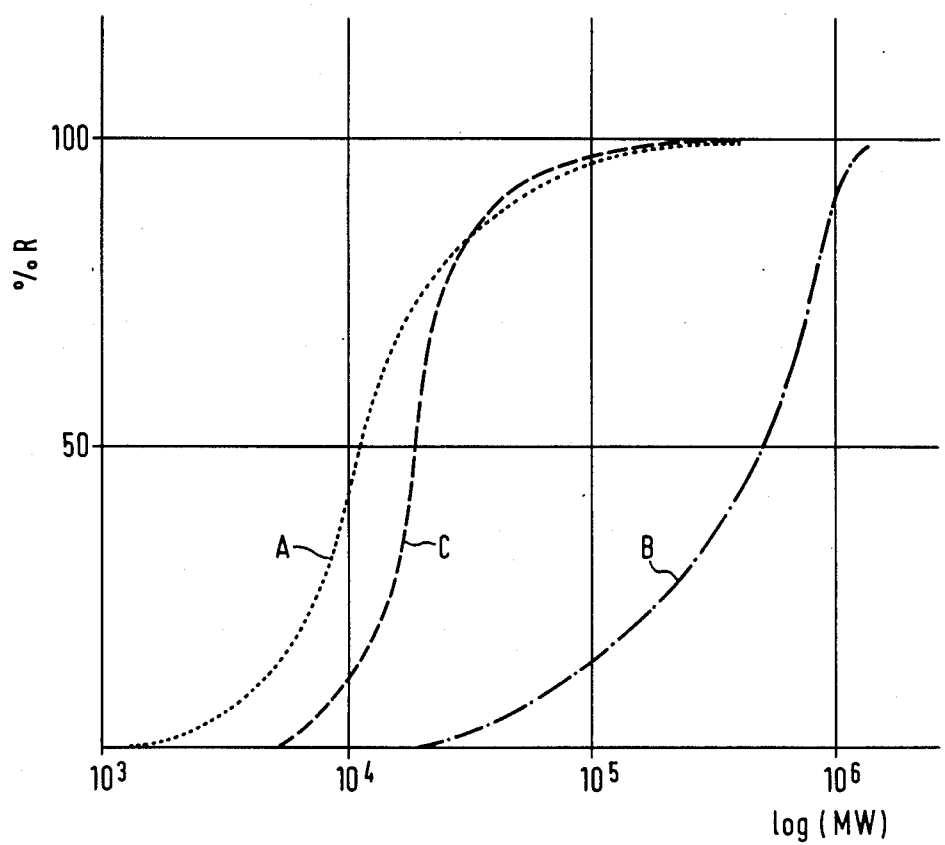
FIG. 1 shows grade efficiency curves for three commerically available membranes.
Figure 2:
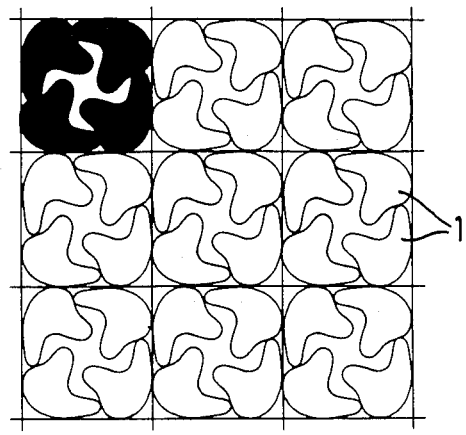
FIGS. 2-4 show protein patterns.
Figure 3:
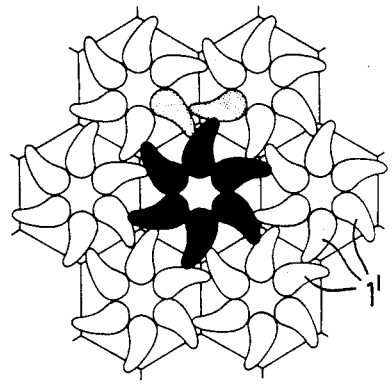
Figure 4:
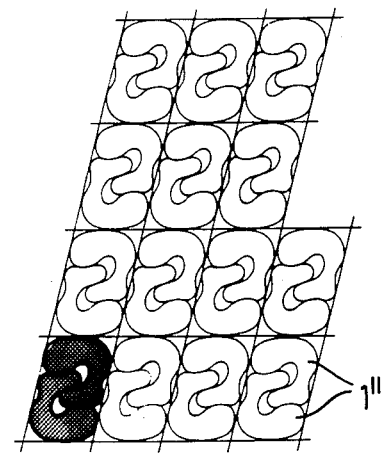

From the surface topography previously determined, it is possible to recognize the type of lattice, which may be quadratic, hexagonal or oblique. FIGS. 2 through 4 show three ideas of patterns, in which one may imagine the S-layers and P-membranes, respectively, of the protein molecules or protein containing molecules, respectively, indicated here by 1, 1' and 1'', to be constructed. FIG. 2 shows a quadratic lattice with p4-symmetry, FIG. 3 a hexagonal lattice with p6-symmetry, and FIG. 4 an oblique lattice with p2-symmetry. Based on these pattern assumptions and since the surface topography of the S-layers and P-membranes also shows recesses arranged according to a lattice, it has been assumed that between the protein molecules or protein containing molecules in the P-membrane, pores remain free, which form continuous openings in the membranes. This assumption has been confirmed, but it will be discussed only further below.

In the following, with the aid of FIGS. 5 of 7, the production of a structure is described in a first example, for the erection of which such P-membranes are used, and which can advantageously be used as an ultrafilter.

EXAMPLE 1

In this example, one starts with the cells of *bacillus stearothermophilus* 3c/NRS 1536, the cell-membrane of which is built up of a cytoplasm membrane, a peptidoglycan containing layer and the S-layer. As is customary in microbiology, the cells are first split open through ultrasonic treatment, the cytoplasm membrane fragments are disintegrated with the aid of detergents, and the remaining cell-membrane fragments are cleaned of the substances contained in the cell by washing. The S-layers are then separated in an aqueous medium by adding 5M guanidine hydrochloride as chaotropic agent from the peptidoglycan containing layer, and brought into solution. This solution is then separated from the peptidoglycan fragments by centrifuging, and the clear solution is dialyzed against a neutral buffer solution containing 10 mM $CaCl_2$ as rinsing liquid. In the course of this dialysis, in which the concentration of guanidine hydrochloride in the solution is reduced to practically zero and the $CaCl_2$-concentration is increased, the P-membranes are created by self-organization, which exhibit a quadratic lattice structure (p4-symmetry) with a periodicity 14 nm and whose maximum dimensions in the facet are about 15 $\mu$m, and which are kept in suspension in the aqueous medium through stirring.

For the production of the ultrafilter, a pressure unit 2, as shown in section in FIG. 5, is used. It is comprised of a bottom part 3, which has a cylindrical groove 4 with a ribbed bottom, in which a porous sinter plate 5 is embedded; the space under the sinter plate 5 is connected to an outlet pipe 7 through an outlet groove 6. A cylindrical wall part 9 of plexiglass is placed on this bottom part 3 by way of an O-sealing ring 8, which wall part is in turn connected to a cover part 11 through a second O-sealing ring 10. In the cover part 11, a supply canal 12 with connections 13, 14 is provided for an inlet pipe or for a pressure gas source, respectively. A magnetic stirring unit 15 is attached to the underside of the cover part 11; with its stirrer 16 it reaches down to the lower edge of the cylindrical wall part 9. For the operation of the pressure unit, the bottom and the cover parts are held together by a clamping device acting at 17 and 17'.

To produce the ultrafilter, a disk-shaped microfilter 18 made by Messrs. Nuclepore, Gottingen, Federal Republic of Germany, is inserted on the sinter plate 5 in the pressure unit, in order to serve as carrier material for the ultrafilter to be produced. This microfilter 18 consists of a polycarbonate film about 10 $\mu$m thick with pores of equal size throughout, with a pore diameter of 0.1 $\mu$m. The above-described P-membrane suspension is then poured into the cover part 11 through connection 13, in such a quantity that 25 $\mu$g P-membrane are contained in the suspension per $cm^2$ area of the microfilter. Thereupon, nitrogen with an overpressure of $0.5 \cdot 10^5$ Pa is introduced as pressure gas through connection 14, whereby the liquid phase of the suspension is pressed through the microfilter 18 and the porous sinter plate 5, and the P-membranes are deposited on the microfilter 18. After the overpressure is discharged, 3 ml of a 2.0% by volume solution of glutardialdehyde (in 0.1M sodium cacodylate buffer, pH 7.2) are applied to the deposited P-membranes through connection 13. Thereafter, a renewed overpressure of $2.10^5$ Pa is created, which causes the glutardialdehyde solution to be pressed for 20 minutes at 20° C. through the deposited P-membranes and the microfilter 18. The glutardialdehyde, whose molecule has a carbonyl group at both ends, thereby reacts as bifunctional cross-linking agent with two $\epsilon$-amino groups of the lysin of the protein containing molecules of the P-membranes, namely either intramolecularly, when both $\epsilon$-amino groups originate from the same protein containing molecule, or intermolecularly, when the two $\epsilon$-amino groups originate from two different protein containing molecules of the P-membranes.

After repeated washing, the ultrafiltration membrane comprised of the microfilter 18 and the deposited and cross-linked P-membranes are then essentially ready and can be removed from the pressure unit 2. However, the pressure unit 2 with the ultrafiltration membrane thusly produced can also be used directly as an ultrafiltration unit.

For the purpose of recording the grade efficiency curve, filtration tests were carried through with this ultrafiltration unit, at an overpressure of $2.10^5$ Pa created through introduced nitrogen, for a series of test molecules at pH-values, in which each of the test molecules were not charged electrically, i.e., at their isoelectric point (IEP). The following proteins served as test substances:

| No. | Protein | Molecular Weight | IEP |
| --- | --- | --- | --- |
| 1 | Myoglobin | 17,000 | 6.6 |
| 2 | Subtilisin | 27,000 | 9.4 |
| 3 | Ovalbumin | 43,000 | 4.6 |
| 4 | Beef serum albumin | 67,000 | 4.7 |
| 5 | Ferritin | 440,000 | 4.3 |

Figure 6:
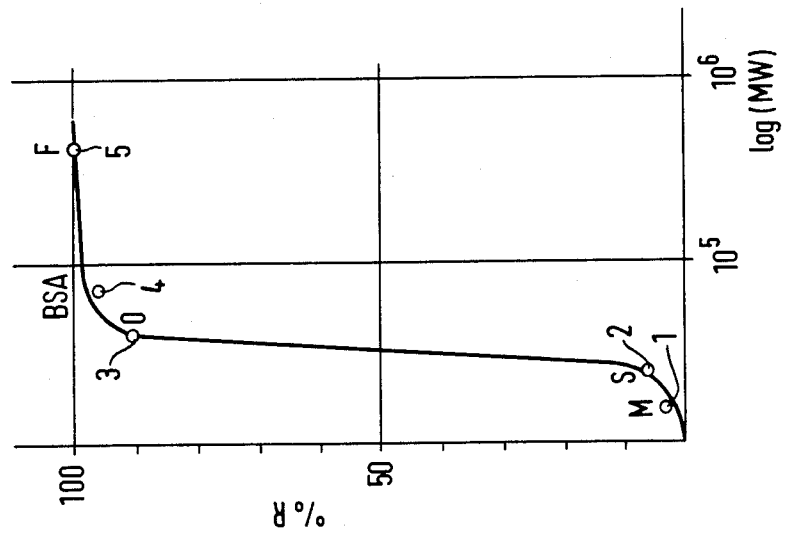
FIG. 6 shows a test value grade efficiency curve.

FIG. 6 shows a diagram with the grade efficiency curve interpolated from the test values for the retention quantities of these test substances. The grade efficiency curve shows a sharp exclusion boundary between the retention quantities of subtilisin and ovalbumin. This grade efficiency curve also proves that the recesses in the surface topography of the P-membrane arranged according to a lattice indeed represent continuous pores of even size; based on the form of the grade efficiency curve, the pore diameter is assumed to be 4–5 nm.

The flow rate determined with this ultrafiltration membrane at a membrane overpressure of $2.10^5$ Pa is about 480 l/h.m². However, the flow rate depends on the quantity of deposited P-membranes. Thus, it drops to a value of 220 l/h.m² with a deposited P-membrane quantity of 50 μg/cm² membrane surface.

The ultrafiltration membrane produced in this manner has an additional advantageous quality, which is explained below in greater detail:

The free amino groups and carboxyl groups contribute in different ways to the electrical net charge of the S-layer fragments or the uncrosslinked P-membranes, respectively, depending on the pH-value of the aqueous medium surrounding them. Up to a pH-value smaller than 9.0, the amino groups produce positive charges, and the carboxyl groups produce negative charges in the range above pH 2.0. At a certain pH-value, i.e., at their isoelectric point (IEP), the negative and positive charges compensate each other, so that the S-layer fragments and the P-membranes will outwardly appear electrically neutral. In the present example, potential positive charge carriers of the P-membranes are lost through the reaction of the glutardialdehyde with the $\epsilon$-amino groups of the lysin of the protein containing molecules of the P-membranes, whereby the IEP of the cross-linked P-membranes is shifted into the acid range and has a value of less than pH 2.0. The negative net charge of the cross-linked P-membranes is in many cases an effective protection against a displacement of the membrane pores in filtrations under physiological conditions.

Figure 7:
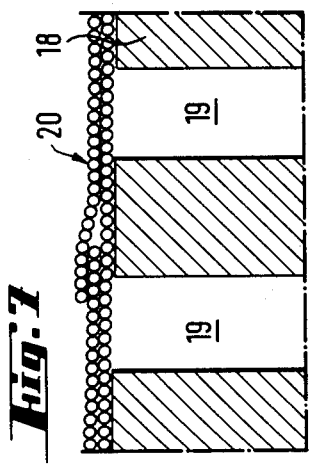
FIGS. 7 and 8 show sectional views of a membrane.

FIG. 7 shows in a partial presentation the utrafiltration membrane produced according to this example, in schematic section. On the surface of microfilter 18 provided with continuous pores 19, the P-membranes indicated with 20 are deposited and fixed through cross-linking. They are thereby applied in such a quantity that the total surface of the P-membrane quantity is equal to about two to three times the area of the ultrafiltration membranes, so that the P-membranes will on average be superposed in about two layers and thereby will overlap in part.

EXAMPLE 2

Deviating from the method according to example 1, one starts in this example with cells of *bacillus stearothermophilus* PV 72. Here, too, the cell-membranes are comprised of a cytoplasm membrane, a peptidoglycan containing layer and a S-layer of protein-containing molecules. Similar to what has been described in example 1, a suspension of P-membranes is produced from the cell-membranes. The S-layer and the P-membranes, respectively, of the cell-membranes of this bacillus exhibit a hexagonal lattice structure (p6 symmetry) with a periodicity of 18 nm.

To produce a structure usable as an ultrafiltration membrane, a disk-shaped nylon microfilter of type Ultipor $N_{66}$ T of Messrs. Pall, . . ., U.S.A., 150 μm thick, is inserted in the pressure unit 2 to serve as carrier. This microfilter has free amino and carboxyl groups in a ratio of 1:1. Similar to the procedure according to example 1, the P-membrane suspension is applied to the microfilter in such a quantity that 30 μg P-membranes are contained in the suspension per cm² microfilter area, and the P-membranes are deposited on and in the spongy structure of the microfilter, respectively, through application of a membrane overpressure of $2.10^5$ Pa.

Figure 8:
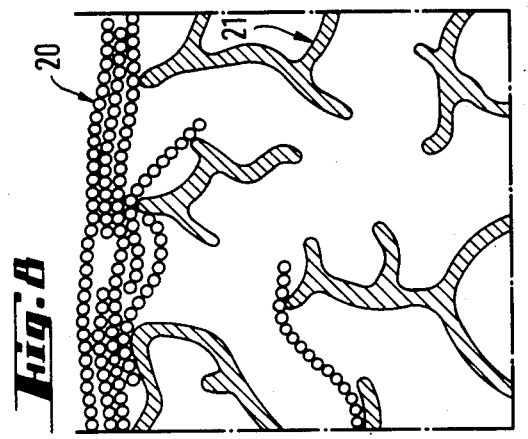

FIG. 8 shows in a partial sectional view the microfilter 21, which has an irregular fiber structure, with the dimensions of the pores left free between the fibers in a random distribution around a mean value. The deposited P-membranes 20 are also shown. Thereupon, at an overpressure of $2.10^5$ Pa, 1 ml of a 0.1% dimethyl suberimidate solution (1M triethanolamine buffer, pH 9.5) is pressed through the P-membranes 20 and the microfilter 21 for 60 minutes at 4° C. The dimethyl suberimidate, as a bifunctional imido ester, thereby reacts like an aldehyde intra- and intermolecularly primarily with the $\epsilon$-amino groups of the lysin of the protein containing molecules of the P-membranes, as well as with the amino groups of the nylon microfilter material. After repeated washing, the ultrafiltration membrane is then ready for use.

Figure 9:
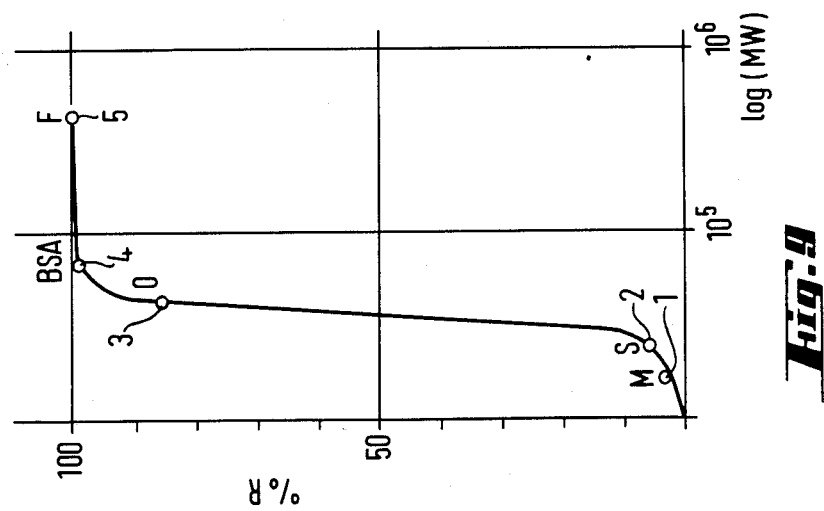
FIG. 9 shows a grade efficiency curve.

FIG. 9 shows the diagram with the grade efficiency curve of the ultrafiltration membrane. It shows a sharp exclusion boundary, similar to the membrane described in example 1.

The amidines created during the reaction of the dimethyl suberimidate with the ε-amino groups produce a positive charge, in a manner similar as the ε-amino group of the lysin, so that the natural net charge of the P-membranes is hardly changed by the cross-linking.

The structures with P-membranes described in the preceding examples 1 and 2, which can advantageously be used as ultrafiltration membranes, have a high chemical and mechanical stability through the cross-linking with bifunctional foreign molecules. In particular, they are stable against a proteolytic degradation, they are autoclavable, and can also be used in an acid and alkaline medium (pH 1 to 13), as well as together with highly concentrated chaotropic agents (5M guanidine hydrochloride, 8M urea).

The desired pore diameter of the ultrafiltration membranes is essentially obtained through the selection of the microorganism to be used, the cell-membranes of which have S-layers with pores of approximately the pore diameter striven for. The desired pore diameter can then be varied through an addition of foreign molecules which reach into the area of the pores of the P-membranes. This will be discussed further below.

P-membranes constructed of one molecule layer exhibit layer thicknesses of about 5 to 20 nm, and pore diameter in the range between 1 and 6 nm.

Regarding the production of the P-membrane suspension it should be noted that through selection of the chaotropic agents and the surfactants, respectively, it is possible to obtain that the S-layer fragments are merely separated from the peptidoglycan containing layer of the cell-membrane fragments, or that the S-layer fragments themselves disintegrate and are brought into solution. For example, if through treatment with 2.5M guanidine hydrochloride only a separation of the S-layer fragments is obtained, a disintegration of the S-layer is achieved with 5M guanidine hydrochloride through rupture of the links between the individual protein molecules or protein containing molecules. A disintegration of the S-layer can also be caused by a substantial change of the pH-value of the solution containing the S-layers; e.g., through lowering the pH-value from about 7.0 to 2.5, or in some cases, by raising it from 7.0 to 9.5.

The facets of the P-membranes created by self-organization can be plane, curved, cylindrical or vesicular in form. According to examples 1 and 2, P-membranes were used, the facets of which were essentially plane.

Figure 10:
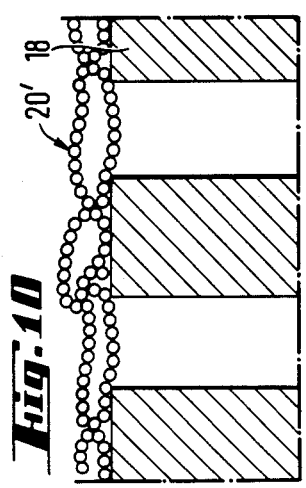

FIGS. 9 and 10 show variants of the structures described in examples 1 and 2, in which the P-membranes 20' are vesicular in form.

Figure 11:
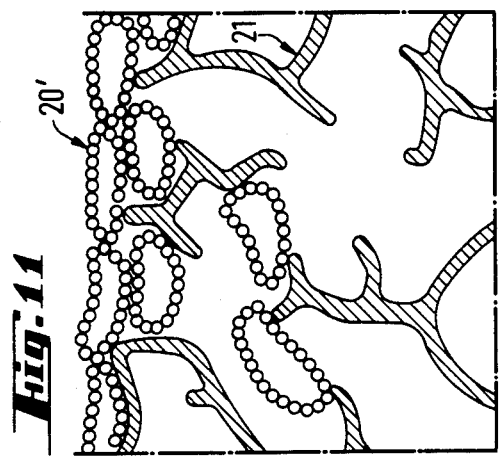

FIG. 11 shows a further variant of the structure according to example 2, in the production of which vesicular and plane shaped P-membranes 20 and 20', respectively, were used. The vesicular P-membranes were deposited mainly in the pores, while the plane P-membranes were preponderantly deposited on the surface of microfilter 21.

A few additional examples for the cross linkage of the P-membranes are described below.

Hexamethylene diisocyanate reacts at the P-membranes preferably with the amino groups and after they are saturated, with the hydroxyl groups, so that an intermolecular cross linkage can take place through both funactional groups. For example, hexamethylene diisocyanate is used in a 1% solution with 5% tetrahydrofuran (triethanolamine hydrochloride, pH 8.0). The reaction time is, e.g., 4 hours at 20° C.

N-N'-Diiodoacetyl-hexamethylene diamine attacks sulfhydryl groups at the P-membranes, as do also other bifunctional alkyl halides, yet under suitable reaction conditions it will also attack the amino groups. In a neutral or weakly alkaline medium, however, this cross-linking agent is specified for the sulfhydryl groups. For cross-linkage, N'N'-diiodoacetyl-hexamethylene diamine is used preferably in a 0.5% solution (0.1M sodium acetate buffer, pH 7.2). The reaction time is 3 hours at 4° C.

1-Ethyl-3-(3 dimethylaminopropyl)-carbodiimide hydrochloride (EDC)

Carbodiimides such as EDC react in an acid medium with the carboxyl, sulfhydryl and hydroxyl groups of tyrosin at the P-membranes. While the reaction with tyrosin proceeds only very slowly, sulfhydryl groups—if they are not to take part in the reaction—must be masked beforehand. By blocking the carboxyl groups with EDC, the natural net charge of the P-membranes is shifted into the acid range. EDC (0.1M distilled water with 0.02M NaOH, pH 8.0), for example, is left to react for 18 hours at room temperature.

Several examples for the addition of foreign molecules to the protein molecules or protein containing molecules of the P-membranes are given below, wherein these foreign molecules appropriately affect the pore size of the cross-linked P-membranes:

The P-membranes deposited on a porous carrier, e.g., a microfilter, are coated with a solution of polycationized ferritin (5 μg polycationized ferritin in 1 ml $H_2O$) and incubated for 5 minutes at 20° C. As could be determined electron microscopically, one ferritin molecule is linked under these conditions with each protein molecule or protein containing molecule through electrostatic interactions. Through a subsequent cross-linkage with glutardialdehyde analogous to the process described in example 1, the ferritin molecules are then covalently linked to the P-membranes.

P-membranes applied to a carrier are coated with a 1% solution of osmium tetroxide and incubated for 30 minutes at 20° C. After the excess solution is washed out, the osmium chemically linked in the P-membranes can be established by electron microscope and with the aid of X-ray analysis. The cross-linking of the P-membranes then takes place according to example 1.

P-membranes applied to a carrier are treated with a bifunctional cross-linking agent, the bridge-length of which is close to the dimension of the pore-diameter of the P-membrane. The following substances can be considered as bifunctional cross-linkage agents with varying bridge-length:

Tardryl-di-(glycylazide) (TDGA): 1.3 nm bridge-length

Tardryl-di-(ε-aminocaproyl azide) (TDCA): 2.3 nm bridge-length

Bis-methyl-3,8-diazo-4,7-dioxo-5,6-dihydroxydecane bisimidate (DEBE): 1.4 nm bridge-length Bis-methyl-4,9-diazo-5,8-dioxo-6,7-dihydroxydodecane bisimidate (DOBE): 1.7 nm bridge-length The reaction of TDGA or TDCA, DEBE or DOBE (0.1M in distilled water with 1M triethanol amine, pH 8.0) takes place for one hour at 4° C. or for 30 minutes at 20° C., and the cross-linking reaction is carried through analogous to the one described in example . . , whereupon cross-linking can take place according to example 1.

EXAMPLE 3

In this Example, a variant of the method according to the invention is described, in which a layer is produced from P-membranes which may have larger surface ranges, in particular, dimensions of up to 100 um, and which consist of a single-layer P-membrane. To this, a suspension is produced from P-membranes, as described in example 1, and which was obtained from cell-membranes of *bacillus stearothermophilus* 3c/NRS 1536. The S-layers of the cell-membranes of this bacillus are electrically neutral at their surfaces adjoining the outside of the cell, while they have a negative net charge at their other surface, at which the carbohydrate remnant of the protein containing molecules (glycoproteins) forming these S-layers is exposed. The aforesaid P-membrane solution contains in addition also a free protein containing molecules of the S-layers in solution. A microfilter with an especially smooth surface, such as was also used according to example 1, is treated at one surface with a solution of Alcian Blue (0.1% in distilled water) and then dried. The Alcian Blue produces in a neutral medium a positive surface charge on the microfilter surface. The P-membrane solution is then applied to the microfilter under light stirring. Then, induced by the positive surface charge, there takes place at some areas of the microfilter surface, a self-organization into P-membranes of the protein molecules or protein containing molecules still in solution, whereby the negatively charged side of the P-membranes adjoins the positively charged microfilter surface, on the one hand, while, on the other hand, the P-membranes in the suspension, which usually may have maximum surface dimensions of up to 15 um, adjoin with their negatively charged side preferably the still free areas of the microfilter surface. To stabilize the thusly formed P-membrane layer, it is cross-linked—in a manner analogous to that described in example 1.

FIG. 13 shows in a partial sectional view the thusly produced structure, which can also advantageously be used as an ultrafiltration membrane, with microfilter 18 and a P-membrane produced at the solid-to-liquid phase boundary through self-organization, for greater surface expansion. In its application as an ultrafiltration membrane, the structure so produced has the same contact boundary and separating capacity as the structure produced according to example 1.

Quite generally and in part deviating from the methods described in examples 1 through 3, it is also possible to use as support surfaces, at which a P-membrane layer is formed, other layers, e.g., peptidoglican containing layers, pseudo layers, lipid layers, polymer layers, gels, and similar. When these layers have continuous pores, the size of which is greater than that of the P-membranes, they can serve as permanent carrier for the P-membrane layers, or they may be auxiliary layers, which are removed after the formation of the P-membrane layer, e.g., by means of organic solvents. The P-membrane layers separated from auxiliary layers may, appropriately after covalent cross-linking, be applied to a final carrier that is better adapted to the requirements of the intended use of the structure according to the invention, with which carrier they may then also be appropriately covalently cross-linked.

The surface characteristics of the "support surface," such as its hydrophilic or hydrophobic nature, and/or the specific net charge and the charge distribution on the "support surface," permit—similar to the method according to example 3—an oriented bond of the P-membranes and/or of the protein molecules or protein containing molecules to the "support layer" and thereby promote the formation of the P-membrane-layer. These surface properties should be such, inter alia, that the bonding strength between the "support surface" and protein molecule or protein containing molecule combined with it is weak enough so as not to prevent the self-organization of these molecules into P-membranes, which is taking place on this "support surface." This is important for the formation of P-membranes with few disturbances in the crystal lattice.

The above described examples and their variants, respectively, are concerned with structures with P-membranes, in which the protein molecules or protein containing molecules are linked to each other in a single layer. FIG. 14 shows schematically, in a partial, sectional view, a further variant of the structure according to the invention, in which, on a porous microfilter such as was also used according to example 2, a P-membrane layer is applied, consisting of P-membranes 22 built-up in mirror-inverted manner of two layers 23, 23' of protein molecules or protein containing molecules. Each of these two layers of molecules 23, 23' is formed differently at its inside and its outside, respectively, and the two layers 23, 23' are linked to each other in such a manner that they occupy the most energy-stable position. The two layers 23, 23' can additionally be covalently cross-linked with other, as can the P-membrane 22 with the microfilter 21, respectively.

In addition to an application as ultrafiltration membrane, the structure according to the invention can also be utilized advantageously as separating organ for a gas separation or as separating organ for an ion exchange process.

In further, advantageous applications, the structure according to the invention serves as carrier for other semipermeable membranes which stretch over the pores of the P-membranes of the structure. These other semi-permeable membranes can be hyperfiltration membranes, in particular mono- or bimolecular hyperfiltration membranes. Such hyperfiltration membranes, particularly surfactant- or surfactant-like lipoid hyperfiltration membranes are generally only 2 to 6 nm thick and are particularly fragile. Hyperfiltration membranes are utilized especially in the areas of seawater desalination, sewage treatment, separation of mixtures of organic liquids, in particular for hydrocarbon separation through pervaporation or for separating optical antipodes by means of chiral separating layers.

FIG. 15 shows in partial sectional view a structure according to the invention, the production of which has been described in example 2 (see FIG. 8), on the P-membrane layer 24 of which the hyper filtration membrane 25 has been applied. In the utilization of the structures according to the invention as carriers of hyperfiltration membranes, the filtering or the separating action, respectively, is essentially determined by the hyperfiltration membrane. Defects, such as small holes or similar in the P-membrane layer 24 are not necessarily troubling. The cross-linked P-membrane layer is particularly suitable as a carrier for the hyperfiltration membranes, since they have sufficient mechanical stability to so stretch over or fill up pores and rough surfaces of the customary carrier layers of ultrafiltration membranes that the fragile hyperfiltration membranes, especially cross-linked monolayers, can be consistently mounted or separated. Furthermore, the M-membrane layers are sufficiently thin to ensure an adequately high rate of flow in combination with the hyperfiltration membranes.

A particularly smooth surface of the P-membrane layer is obtained especially with the aid of the following method. Similar to what has been described in example 1, a P-membrane layer is produced and cross-linked on a polycarbonate carrier with a very smooth surface. The polycarbonate carrier is then dissolved in chloroform, whereby a cohesive P-membrane layer 5–100 nm thick is left, which is then deposited with its original very smooth bottom side up onto another porous carrier. On this very smooth exposed surface of the P-membrane layer, the hyperfiltration membrane is then deposited and appropriately cross-linked with the P-membrane layer.

Compounds of a P-membrane layer and a hyperfiltration membrane can also be produced, in that on a hyperfiltration membrane that has a defined surface net charge serving as "support surface"—e.g., analogous to what has been described with the aid of example 3—a membrane layer is formed and the latter is appropriately cross-linked with the hyperfiltration membrane.

For a covalent cross-linking between the hyperfiltration membranes and the P-membrane layers those reactions may be considered above all, in which carboxyl, hydroxyl, amino and sulfhydryl groups participate. With P-membranes of glycoprotein and single-layer hyperfiltration membranes with sugar residues, carbohydrate chemical reactions may also be used.

Compounds of a P-membrane layer and a hyperfiltration membrane can furthermore serve themselves as carrier or "support surface" for additional hyperfiltration membranes or P-membrane layers. Such multilayer compounds can also be cross-linked in the plane of the single layers or also between the single layers, through covalent bonds. The formation of a sandwich compound consisting of two hyperfiltration membranes at both sides of a P-membrane layer permits the interleaving of foreign molecules, such as enzymes or charge carriers, which can substantially influence the behavior of such a sandwich compound.

The aforesaid compounds or multilayer compounds, respectively, can advantageously also take the form of closed vesicles, in the production of which one may start with a "starting vesicle" consisting of a hyperfiltration membrane or of a P-membrane layer.

In a further advantageous application, the structure according to the invention is used as separating column for penetration chromatography. FIG. 16 shows schematically in a partial sectional view such a chromatography column 26, in which vesicular, appropriately intra- or intermolecularly cross-linked P-membranes 22' with an inside diameter in the range of 1 to 5 m have been filled in. The substances to be separated are fed in at the top of the column, After the substances are passed through and eluted, the larger molecules emerge at the lower end of the chromatography column earlier than the smaller molecules, with the chromatography showing a very sharp fractionation in the range of the pore-size of the P-membranes.

According to an advantageous variant, the flow rates through the separating column can be increased in that the P-membrane vesicles 22' are combined covalently cross-linked in morphologically defined and mechanically stable aggregates. To produce these aggregates, a dense pellet (sediment) of P-membrane vesicles is quick-frozen in a thin layer, pulverized into small fragments under liquid nitrogen and subsequently freeze-substituted in a mixture of methanol and glutardialdehyde at, e.g., −80° C., whereat the cross-linking takes place with the aid of the glutardialdehyde. The aggregates so obtained can be fragmented still further, sifted by size categories, with only specific size categories of the aggregates to be used for filling the separating column. In addition, either before or after the column is filled, the aggregates can be transformed into buffers and/or chemical or enzymatic changes of the aggregates can be effected.

In a last advantageous application, the structure according to the invention is used as envelope material for substances. This envelope material may be a cross-linked P-membrane layer which, as described above, is produced on an auxiliary layer or "support surface," whereupon the auxiliary layer is appropriately removed. The films thusly produced can advantageously be used as packaging material and as such have the advantage in that they are biologically degradable, and the degradation speed can be influenced by the type and degree of the covalent cross-linking.

P-membrane layers of this type can finally also find application as capsule-envelopes for pharmaceutical preparations administered orally, whereby the desired release of the content is caused only by the proteolytic degradation in specific sections of the digestive tract. By a selective chemical change of the P-membrane layers of the envelope membranes, their speed of degradation and thereby the time of release of the capsule contents can be determined. The release of the capsule content may take place already before the P-membrane layer is dissolved, for which it is controlled by the pore-size. Moreover, pH-effects can also induce the release.

| LIST OF REFERENCES | |
|---|---|
| 1, 1', 1'' | Molecules |
| 2 | Pressure unit |
| 3 | Bottom part |
| 4 | Groove |
| 5 | Sinter plate |
| 6 | Outlet groove |
| 7 | Outlet pipe |
| 8 | O—sealing ring |
| 9 | Wall part |
| 10 | O—sealing ring |
| 11 | Cover part |
| 12 | Supply canal |
| 13, 14 | Connections |
| 15 | Magnetic stirring unit |
| 16 | Stirrer |
| 17, 17' | Position (for action of clamping device) |
| 18 | Microfilter |
| 19 | Pores (of 18) |
| 20, 20', 20'' | P—membranes |
| 21 | Microfilter |
| 22 | Double P—membranes |
| 23, 23' | (Single) Layers (of 22) |
| 24 | P—membrane layer |
| 25 | Hyperfiltration membrane |
| 26 | Separating column |

We claim:

1. A structure which comprises at least one membrane with continuous pores having a diameter within the range of 1 to 8 nm, extending along plane, curved, cylindrical or vesicular surfaces consisting essentially of at least one layer of contiguous identical protein containing molecules, which molecules are arranged to form a crystal lattice defining continuous pores free of the said molecules, the membrane being connected to a support layer or the membranes being connected together to form a stable unsupported film.

2. A structure according to claim 1 wherein the membrane is connected to an appropriate porous carrier.

3. A structure of claim 1 wherein the protein containing molecules are derived from the S-layer of the cell envelopes or cell walls of prokaryotes.

4. The structure of claim 3 wherein the membrane is comprised of P-membranes.

5. A structure of claim 1 wherein the membranes formed by the protein containing molecules are arranged in several contiguous layers, each according to a crystal lattice and joined to each other.

6. A structure of claim 1 wherein the contiguous protein containing molecules in the layers are linked to each other by secondary valence bonds.

7. A structure of claim 1 wherein mono- or bifunctional foreign molecules are linked to reactive groups of the protein containing molecules.

8. A structure of claim 7 wherein the reactive groups are at least one member selected from the group consisting of carboxyl, amino, sulfhydryl and hydroxyl.

9. A structure of claim 7 wherein the foreign molecules are linked to essentially all the protein containing molecules at the same reactive places.

10. A structure of claim 9 wherein the protein containing molecules of the membrane are at least one of intermolecularly and intra-molecularly covalently crosslinked through bifunctional foreign molecules.

11. A structure of claim 7 wherein the foreign molecules extend into a zone of the membrane pores recessed between the protein containing molecules.

12. A structure of claim 7 wherein the foreign molecules linked to the protein containing molecules have dissociable groups which dissociate under the working conditions of the structure and can thereby accept predetermined electric charges depending upon the specific working conditions.

13. A structure of claim 12 wherein the electric charges on the two surfaces that are parallel to the extension of the membrane are different.

14. A structure of claim 1 wherein membranes on which contiguous or neighboring protein containing molecules belonging to the same or different membranes are covalently cross linked to each other by bifunctional foreign molecules.

15. A structure of claim 1 wherein the membranes of the protein containing molecules are connected to a support layer and are crosslinked to the support material by bifunctional foreign molecules.

16. A structure of claim 1 wherein the protein containing molecules have dissociable groups which dissociate under the working conditions of the structure and can thereby accept predetermined electric charges depending upon the specific working conditions.

17. A structure of claim 16 wherein the electric charges on the two surfaces that are parallel to the extension of the membrane are different.

18. A structure of claim 1 wherein the protein containing molecules of the membranes are at least one of intermolecularly and intramolecularly covalently cross linked.

19. A method for producing a structure of claim 1 comprising suspending or dissolving protein containing molecules or fragments obtained from cell envelopes or cell walls of microorganisms or fragments of S-layers of such cells in a liquid medium, combining the protein containing molecules or the layer fragments through self organization into a membrane with a crystal lattice having continuous pores free of the protein containing molecules and either placing the membrane with a lattice onto a support layer or connecting the membranes together to form a stable unsupported film.

20. The method of claim 19 wherein the protein containing molecules of the membranes are crosslinked intra-molecularly with at least one of each other and the carrier.

21. The method of claim 19 wherein the crosslinked lattice is removed from the support layer.

22. The method of claim 19 wherein the combining of the protein containing molecules is effected by changing the pH value.

23. The method of claim 19 wherein the self organization of the molecules is effected by reducing the concentration of chaotropic agent in the medium.

24. The method of claim 19 wherein the membranes are treated with at least one of monofunctional and bifunctional foreign molecules which are linked to reactive groups of the protein containing molecules.

25. A method of claim 24 wherein the reactive groups are at least one member selected from the group consisting of carboxyl, amino, sulfhydryl and hydroxyl.

26. The method of claim 19 wherein the protein containing molecules are derived from cell walls or cell envelopes of microorganisms or fragments thereof.

27. The method of claim 19 wherein the pH value of the solution or suspension is increased from about 7.0 to a value not more than 13.0 before combining.

28. The method of claim 27 wherein the pH value is increased from 7.0 to not more than 9.5.

29. The method of claim 27 wherein the combining of the molecules by self organization is effected by adjusting the pH of the liquid medium to approximately 7.

30. The method of claim 19 wherein the pH value of the solution or suspension is decreased by reducing the pH value from 7 to not less than 1.0 before combining.

31. The method of claim 30 wherein the combining of the molecules by self organization is effected by adjusting the pH of the liquid medium to approximately 7.

32. The method of claim 19 wherein the self organization of the protein containing molecules or layer fragments is effected at a solid-to-liquid phase boundary.

33. The method of claim 19 wherein the protein containing molecules combined by self organization have all maximum area dimensions of less than 100 μm.

34. The method of claim 19 wherein the membrane is deposited on a porous support layer.

35. The method of claim 19 wherein the combining of the molecules by self organization is effected by adjusting the pH of the liquid medium to approximately 7.

36. The method of claim 19 wherein said liquid medium contains chaotropic agents.

* * * * *